US010620232B2

(12) United States Patent
Tu et al.

(10) Patent No.: US 10,620,232 B2
(45) Date of Patent: Apr. 14, 2020

(54) DETECTING CONTROLLERS IN VEHICLES USING WEARABLE DEVICES

(71) Applicant: Apple Inc., Cupertino, CA (US)

(72) Inventors: Xiaoyuan Tu, Cupertino, CA (US); Anil K. Kandangath, Cupertino, CA (US); Adam S. Howell, Cupertino, CA (US)

(73) Assignee: Apple Inc., Cupertino, CA (US)

( * ) Notice: Subject to any disclaimer, the term of this patent is extended or adjusted under 35 U.S.C. 154(b) by 352 days.

(21) Appl. No.: 15/273,038

(22) Filed: Sep. 22, 2016

(65) Prior Publication Data

US 2017/0082649 A1 Mar. 23, 2017

Related U.S. Application Data

(60) Provisional application No. 62/221,903, filed on Sep. 22, 2015.

(51) Int. Cl.
*G01P 13/00* (2006.01)
*A61B 5/00* (2006.01)
*A61B 5/11* (2006.01)
*A61B 5/18* (2006.01)

(52) U.S. Cl.
CPC ................... *G01P 13/00* (2013.01)

(58) Field of Classification Search
CPC . G01P 13/00; A61B 5/681; A61B 5/18; A61B 5/1118
See application file for complete search history.

(56) References Cited

U.S. PATENT DOCUMENTS

| | | |
|---|---|---|
| 4,566,461 A | 1/1986 | Lubell et al. |
| 5,158,093 A | 10/1992 | Shvartz et al. |
| 5,663,897 A | 9/1997 | Geiser |
| 6,013,008 A | 1/2000 | Fukushima |
| 6,059,724 A | 5/2000 | Campell et al. |
| 6,582,380 B2 | 6/2003 | Kazlausky et al. |
| 6,687,535 B2 | 2/2004 | Hautala et al. |
| 6,837,827 B1 | 1/2005 | Lee et al. |
| 7,254,516 B2 | 8/2007 | Case, Jr. et al. |
| 7,311,675 B2 | 12/2007 | Peifer et al. |
| 7,467,060 B2 | 12/2008 | Kulach et al. |

(Continued)

FOREIGN PATENT DOCUMENTS

| | | | |
|---|---|---|---|
| GB | 2465824 A | | 6/2010 |
| IN | 259/KOL/2015 | * | 12/2015 |

(Continued)

OTHER PUBLICATIONS

Novatel, "IMU Error and Their Effects", Novatel Application Notes APN-064 Rev A p. 1-6, Feb. 21, 2014.*

(Continued)

*Primary Examiner* — Catherine T. Rastovski
(74) *Attorney, Agent, or Firm* — DLA Piper LLP US

(57) ABSTRACT

In one aspect, the present disclosure relates to a method, including determining, by a wearable device, receiving, by a wearable device, motion information from a motion sensor of the wearable device, determining, by the wearable device using the motion information, that a vehicle is turning, and determining, by the wearable device using the motion information when the vehicle is turning, that a user of the wearable device is controlling the vehicle.

16 Claims, 10 Drawing Sheets

(56) References Cited

U.S. PATENT DOCUMENTS

| | | |
|---|---|---|
| 7,534,206 B1 | 5/2009 | Lovitt et al. |
| 7,690,556 B1 | 4/2010 | Kahn et al. |
| 7,771,320 B2 | 8/2010 | Riley et al. |
| 7,805,149 B2 | 9/2010 | Werner et al. |
| 7,841,967 B1 | 11/2010 | Kahn et al. |
| 8,290,480 B2 | 10/2012 | Abramson et al. |
| 8,483,775 B2 | 7/2013 | Buck et al. |
| 8,589,174 B2 | 11/2013 | Nelson et al. |
| 8,892,391 B2 | 11/2014 | Tu et al. |
| 8,894,576 B2 | 11/2014 | Alwan et al. |
| 8,911,329 B2 | 12/2014 | Lin et al. |
| 9,413,871 B2 * | 8/2016 | Nixon ............... H04M 1/72527 |
| 9,526,430 B2 | 12/2016 | Srinivas et al. |
| 9,788,794 B2 | 10/2017 | LeBoeuf et al. |
| 10,188,347 B2 | 1/2019 | Self et al. |
| 10,206,627 B2 | 2/2019 | LeBoeuf et al. |
| 10,219,708 B2 | 3/2019 | Altini |
| 10,290,260 B2 | 5/2019 | Wu et al. |
| 10,292,606 B2 | 5/2019 | Wisbey et al. |
| 2001/0022828 A1 | 9/2001 | Pyles |
| 2002/0019585 A1 | 2/2002 | Dickinson |
| 2003/0032460 A1 | 2/2003 | Cannon et al. |
| 2004/0064061 A1 | 4/2004 | Nissila |
| 2005/0107723 A1 | 5/2005 | Wehman et al. |
| 2006/0064277 A1 | 3/2006 | Jung et al. |
| 2006/0136173 A1 | 6/2006 | Case et al. |
| 2006/0190217 A1 | 8/2006 | Lee et al. |
| 2006/0217231 A1 | 9/2006 | Parks et al. |
| 2007/0100666 A1 | 5/2007 | Stivoric et al. |
| 2007/0150229 A1 | 6/2007 | Fujiwara |
| 2007/0219059 A1 | 9/2007 | Schwartz et al. |
| 2007/0275825 A1 | 11/2007 | O'Brien |
| 2007/0276271 A1 | 11/2007 | Chan |
| 2008/0096726 A1 | 4/2008 | Riley et al. |
| 2008/0214360 A1 | 9/2008 | Stirling et al. |
| 2009/0009320 A1 | 1/2009 | O'Connor et al. |
| 2009/0024332 A1 | 1/2009 | Karlov et al. |
| 2009/0043531 A1 | 2/2009 | Kahn et al. |
| 2009/0063099 A1 | 3/2009 | Counts et al. |
| 2010/0030350 A1 | 2/2010 | House et al. |
| 2010/0130890 A1 | 5/2010 | Matsumura et al. |
| 2010/0184564 A1 | 7/2010 | Molyneux et al. |
| 2010/0204952 A1 | 8/2010 | Irlam et al. |
| 2010/0210953 A1 | 8/2010 | Sholder et al. |
| 2010/0210975 A1 | 8/2010 | Anthony, III et al. |
| 2010/0217099 A1 | 8/2010 | Leboeuf et al. |
| 2010/0274102 A1 | 10/2010 | Teixeira |
| 2010/0298656 A1 | 11/2010 | McCombie et al. |
| 2011/0040193 A1 | 2/2011 | Seppanen et al. |
| 2011/0054359 A1 | 3/2011 | Sazonov et al. |
| 2011/0082008 A1 | 4/2011 | Cheung et al. |
| 2011/0131012 A1 | 6/2011 | Czaja et al. |
| 2011/0152695 A1 | 6/2011 | Granqvist et al. |
| 2011/0195707 A1 | 8/2011 | Faerber et al. |
| 2011/0238485 A1 | 9/2011 | Haumont et al. |
| 2011/0301436 A1 | 12/2011 | Teixeira |
| 2012/0083715 A1 | 4/2012 | Yuen et al. |
| 2012/0172677 A1 | 7/2012 | Logan et al. |
| 2012/0238832 A1 | 9/2012 | Jang et al. |
| 2012/0296455 A1 | 11/2012 | Ohnemus et al. |
| 2012/0322621 A1 | 12/2012 | Bingham et al. |
| 2013/0023739 A1 | 1/2013 | Russel |
| 2013/0041590 A1 | 2/2013 | Burich et al. |
| 2013/0053990 A1 | 2/2013 | Ackland |
| 2013/0096943 A1 | 4/2013 | Carey et al. |
| 2013/0158686 A1 | 6/2013 | Zhang et al. |
| 2013/0178335 A1 | 7/2013 | Lin et al. |
| 2013/0197377 A1 | 8/2013 | Takahiko et al. |
| 2013/0218053 A1 | 8/2013 | Kaiser et al. |
| 2013/0267794 A1 | 10/2013 | Fernstrom et al. |
| 2014/0073486 A1 | 3/2014 | Ahmed et al. |
| 2014/0087708 A1 | 3/2014 | Kalita et al. |
| 2014/0088444 A1 | 3/2014 | Saalasti et al. |
| 2014/0107932 A1 | 4/2014 | Luna |
| 2014/0109390 A1 | 4/2014 | Manning |
| 2014/0167973 A1 | 6/2014 | Letchner et al. |
| 2014/0172238 A1 | 6/2014 | Craine |
| 2014/0197946 A1 | 7/2014 | Park et al. |
| 2014/0200906 A1 | 7/2014 | Bentley et al. |
| 2014/0207264 A1 | 7/2014 | Quy |
| 2014/0213920 A1 | 7/2014 | Lee |
| 2014/0221854 A1 | 8/2014 | Wai |
| 2014/0228649 A1 | 8/2014 | Rayner et al. |
| 2014/0244071 A1 | 8/2014 | Czaja et al. |
| 2014/0266789 A1 * | 9/2014 | Matus ............... H04Q 9/00 340/870.07 |
| 2014/0276127 A1 | 9/2014 | Ferdosi et al. |
| 2014/0278139 A1 | 9/2014 | Hong et al. |
| 2014/0278229 A1 | 9/2014 | Hong et al. |
| 2014/0316305 A1 | 10/2014 | Venkatraman et al. |
| 2014/0348367 A1 | 11/2014 | Vavrus et al. |
| 2015/0087929 A1 | 3/2015 | Rapoport et al. |
| 2015/0088006 A1 | 3/2015 | Rapoport et al. |
| 2015/0100141 A1 | 4/2015 | Hughes |
| 2015/0119728 A1 | 4/2015 | Blackadar et al. |
| 2015/0148632 A1 | 5/2015 | Benaron |
| 2015/0250417 A1 | 9/2015 | Cheng et al. |
| 2015/0256689 A1 | 9/2015 | Erkkila et al. |
| 2015/0260514 A1 | 9/2015 | Menelas et al. |
| 2015/0327804 A1 | 11/2015 | Lefever et al. |
| 2015/0328523 A1 | 11/2015 | Heling et al. |
| 2015/0338926 A1 * | 11/2015 | Park ............... G06F 3/011 345/156 |
| 2015/0345985 A1 | 12/2015 | Fung et al. |
| 2015/0357948 A1 | 12/2015 | Goldstein |
| 2015/0374240 A1 | 12/2015 | Lee |
| 2016/0021238 A1 * | 1/2016 | Abramson ............ H04W 48/04 455/418 |
| 2016/0057372 A1 | 3/2016 | Raghuram et al. |
| 2016/0058302 A1 | 3/2016 | Raghuram et al. |
| 2016/0058329 A1 | 3/2016 | Srinivas |
| 2016/0058332 A1 | 3/2016 | Tan et al. |
| 2016/0058333 A1 | 3/2016 | Arnold et al. |
| 2016/0058356 A1 | 3/2016 | Raghuram et al. |
| 2016/0058370 A1 | 3/2016 | Raghuram et al. |
| 2016/0058371 A1 | 3/2016 | Singh Alvarado et al. |
| 2016/0058372 A1 | 3/2016 | Raghuram et al. |
| 2016/0059079 A1 | 3/2016 | Watterson |
| 2016/0166178 A1 | 6/2016 | Fuss et al. |
| 2016/0170998 A1 | 6/2016 | Frank et al. |
| 2016/0206248 A1 | 7/2016 | Sartor et al. |
| 2016/0256058 A1 | 9/2016 | Pham et al. |
| 2016/0269572 A1 | 9/2016 | Erkkila et al. |
| 2016/0287177 A1 | 10/2016 | Huppert et al. |
| 2016/0361020 A1 | 12/2016 | LeBoeuf et al. |
| 2016/0363449 A1 | 12/2016 | Metzler et al. |
| 2016/0374614 A1 * | 12/2016 | Cavallaro ............ A61B 5/6898 702/181 |
| 2017/0007166 A1 | 1/2017 | Roovers et al. |
| 2017/0074897 A1 | 3/2017 | Mermel et al. |
| 2017/0082649 A1 | 3/2017 | Tu et al. |
| 2017/0094450 A1 | 3/2017 | Tu et al. |
| 2017/0111768 A1 | 4/2017 | Smith et al. |
| 2017/0188893 A1 | 7/2017 | Venkatraman et al. |
| 2017/0202486 A1 | 7/2017 | Martikka et al. |
| 2017/0251972 A1 | 9/2017 | Jayaraman et al. |
| 2017/0259116 A1 | 9/2017 | Mestas |
| 2017/0273619 A1 | 9/2017 | Alvarado et al. |
| 2017/0347885 A1 | 12/2017 | Tan et al. |
| 2017/0367658 A1 | 12/2017 | LeBoeuf et al. |
| 2018/0049694 A1 | 2/2018 | Singh Alvarado et al. |
| 2018/0050235 A1 | 2/2018 | Tan et al. |
| 2018/0055375 A1 | 3/2018 | Martinez et al. |
| 2018/0055439 A1 | 3/2018 | Pham et al. |
| 2018/0056123 A1 | 3/2018 | Narasimha Rao et al. |
| 2018/0056128 A1 | 3/2018 | Narasimha Rao et al. |
| 2018/0056129 A1 | 3/2018 | Narasimha Rao et al. |

FOREIGN PATENT DOCUMENTS

| | | | |
|---|---|---|---|
| JP | | 2010-051333 A | 3/2010 |
| JP | | 2013-39316 A | 2/2013 |
| JP | | 2014-42757 A | 3/2014 |

(56) References Cited

FOREIGN PATENT DOCUMENTS

| JP | 2016-150018 A | 8/2016 |
| --- | --- | --- |
| JP | 2018-000543 A | 1/2018 |
| JP | 2018-015187 A | 2/2018 |
| WO | 2010/090867 A2 | 8/2010 |
| WO | 2011/105914 A1 | 9/2011 |
| WO | 2015/126182 A | 8/2015 |
| WO | 2015/200900 A1 | 12/2015 |
| WO | 2016/044831 A1 | 3/2016 |
| WO | WO2016073620 * | 5/2016 |

OTHER PUBLICATIONS

McArdle, W.D et al., "Exercise Physiology: Nutrition, Energy and Human Performance," Seventh Edition, Lippincott Williams & Wilkins, 2010, pp. 118-198.*
Chu, In-Vehicle Driver Detection Using Mobile Phone Sensors, Submitted for Graduation with departmental Distintion in Electrical and Computer Engineering, Apr. 20, 2011, pp. 1-21.
Bo et al, TEXIVE: Detecting Drivers Using Pwersonal Smart Phones by Beveraging Inertial Sensors, Department of Computer Science, Illinois Institute of Technology, Chicago IL, Dec. 7, 2014, pp. 1-12.
U.S. Appl. No. 15/692,726, 2018-0056123, filed Aug. 31, 2017, Published.
U.S. Appl. No. 15/692,237, 2018-0056129, filed Aug. 31, 2017, Published.
U.S. Appl. No. 15/692,736, 2018-0055375, filed Aug. 31, 2017, Published.
U.S. Appl. No. 15/689,113, 2018-0055439, filed Aug. 29, 2017, Published.
U.S. Appl. No. 15/679,538, 2018-0050235, filed Aug. 17, 2017, Published.
U.S. Appl. No. 15/678,645, 2018-0049694, filed Aug. 16, 2017, Published.
U.S. Appl. No. 15/616,135, 2017-0347885, filed Jun. 7, 2017, Published.
U.S. Appl. No. 15/611,010, Yet to Published, filed Jun. 1, 2017, Pending.
U.S. Appl. No. 15/466,397, 2017-0273619, filed Mar. 22, 2017, Published.
U.S. Appl. No. 15/273,054, 2017-0094450, filed Sep. 22, 2016, Published.
U.S. Appl. No. 15/691,245, 2018-0056128, filed Aug. 30, 2017, Published.
U.S. Appl. No. 15/364,976, 2017-0074897, filed Sep. 14, 2016, Published.
U.S. Appl. No. 15/061,653, 2016-0256058, filed Mar. 4, 2016, Published.
U.S. Appl. No. 14/501,930, 2016-0058329, filed Sep. 30, 2014, Issued.
U.S. Appl. No. 14/502,827, 2016-0058302, filed Sep. 30, 2014, Published.
U.S. Appl. No. 14/501,701, 2016-0058332, filed Sep. 30, 2014, Published.
U.S. Appl. No. 14/502,809, 2016-0058333, filed Sep. 30, 2014, Published.
U.S. Appl. No. 14/502,781, 2016-0058372, filed Sep. 30, 2014, Published.
U.S. Appl. No. 14/502,754, 2016-0058371, filed Sep. 30, 2014, Published.
U.S. Appl. No. 14/501,771, 2016-0058370, filed Sep 30, 2014, Published.
U.S. Appl. No. 14/493,178, 2015-0087929, filed Sep. 22, 2014, Published.
U.S. Appl. No. 14/145,042, 2015-0088006, filed Dec. 31, 2013, Published.
U.S. Appl. No. 14/501,634, 2016-0058356, filed Sep. 30, 2014, Published.

PCT International Application No. PCT/US2017/049693, International Search Report dated Aug. 12, 2017, 3 pages.
Your Fitness FAQ, Why is it important to warm up and cool down in a workout?, 2012, Web, Retrieved from: http://www.yourfitnessfaq.com/whyisitimportanttowarmupandcooldowninaworkout.html.
Vella et al, Exercise After-Burn: Research Update, 2005, Web, Retrieved from: http://www.unm.edu/~lkravitz/Article%20folder/epocarticle.html.
Song et al., "Training Activity Recognition Systems Online Using Real-Time Crowdsourcing", University of Rochester Computer Science, UbiCom' 12, Sep. 5-8, 2012 (2 pages).
Rowlands et al., "Assessing Sedentary Behavior with the GENEActiv: Introducing the Sedentary Sphere". Medicine and science in sports and exercise 46.6 (2014): 1235-1247.
Hasson et al., "Accuracy of four resting metabolic rate production equations: Effects of sex, body mass index, age, and race/ethnicity", Journal of Science and Medicine in Sport, 2011, vol. 14, p. 344-351.
Lucas et al., "Mechanisms of orthostatic intolerance following very prolonged exercise", 2008, J Appl Physiol, 105: 213-225.
Kunze et al., "Where am I: Recognizing on-body positions of wearable sensors." Location-and context-awareness. Springer Berlin Heidelberg, 2005. 264-275.
Keytel et al., "Prediction of energy expenditure from heart rate monitoring during submaximal exercise", 2005, Journal of Sports Sciences, 23(3):289-97.
Sabatini, Kalman-filter orientation determination using inertial/magnetic sensors: observability analysis and performance evaluation, Sep. 27, 2011, Sensors 2011, 11, 9182-9206.
Jackson et al., "Prediction of functional aerobic capacity without exercise testing", Medicine and Science in Sports and Exercise, 22(6), 863-870, 1990.
Isaacs et al., "Modeling energy expenditure and oxygen consumption in human exposure models: accounting for fatigue and EPOC", 2008, Journal of Exposure Science and Environmental Epidemiology, 18: 289-298.
Human Kinetics, Aerobic Workout Components, 2011, Web, Retrieved from: http://www.humankinetics.com/excerpts/excerpts/aerobicworkoutcomponentsexcerpt.
Gao et al., "Evaluation of accelerometer based multi-sensor versus single-sensor activity recognition systems." Medical engineering & physics 36.6 (2014): 779-785.
Frankenfield et al., "Comparison of Predictive Equations for Resting Metabolic Rate in Healthy Nonobese and Obese adults: A systematic review". Journal of the American Dietetic Association. May 2005, vol. 105, No. 5, p. 775-789.
Brooks, G.A. et al., "Exercise Physiology: Human Bioenergetics and Its Applications," Fourth Edition, McGraw Hill, ISBN 0-07-255642-0, Chapter 2: Bioenergetics, Chapter 10: Metabolic Response to Exercise: Lactate Metabolism During Exercise and Recovery, Excess Postexercise O2 Consumption (EPOC), O2 Deficit, O2 Debt, and the Anaerobic Threshold, Chapter 16: Cardiovascular Dynamics During Exercise, Chapter 21: Principles of Endurance Conditioning, Chapter 27: Exercise Testing and Prescription, 141 pages (2004).
Bruce, R.A. et al., "Exercising testing in adult normal subjects and cardiac patients," Pediatrics, vol. 32, No. Suppl., pp. 742-756 (Oct. 1963).
Bruce, R.A. et al., "Maximal oxygen intake and nomographic assessment of functional aerobic impairment in cardiovascular disease," American Heart Journal, vol. 85, Issue 4, pp. 546-562 (Apr. 1973).
Burke, Edmund R., "High-Tech Cycling," Second Edition, Human Kinetics, Chapter 4: Optimizing the Crank Cycle and Pedaling Cadence, Chapter 5: Cycling Biomechanics, Chapter 6: Cycling Power, Chapter 10: Physiology of Professional Road Cycling, Chapter 11: Physiology of Mountain Biking, 131 pages (2003).
Cavanagh, P.R. et al., "The effect of stride length variation on oxygen uptake during distance running," Medicine and Science in Sports and Exercise, vol. 14, No. 1, pp. 30-35 (1982).

(56) References Cited

OTHER PUBLICATIONS

Earnest, C.P. et al., "Cross-sectional association between maximal estimated cardiorespiratory fitness, cardiometabolic risk factors and metabolic syndrome for men and women in the Aerobics Center Longitudinal Study," Mayo Clin Proceedings, vol. 88, No. 3, pp. 259-270, 20 pages (Mar. 2013).
Fox, S.M. et al., "Physical Activity and the Prevention of Coronary Heart Disease," Bull. N.Y. Acad. Med., vol. 44, No. 8, pp. 950-967 (Aug. 1968).
Glass, S., et al., "ACSM's Metabolic Calculations Handbook," Lippincott Williams & Wilkins, 124 pages (2007).
Lavie, C.J. et al., "Impact of cardiorespiratory fitness on the obesity paradox in patients with heart failure," Mayo Clinic Proceedings, vol. 88, No. 3, pp. 251-258 (Mar. 2013).
Margaria, R. et al., "Energy cost of running," Journal of Applied Physiology, vol. 18, No. 2, pp. 367-370 (Mar. 1, 1963).
McArdle, W.D. et al., "Exercise Physiology: Nutrition, Energy and Human Performance," Seventh Edition, Lippincott Williams & Wilkins, published 2010, pp. 118-198.
Myers, J. et al., "Exercise Capacity and Mortality Among Men Referred for Exercise Testing," The New England Journal of Medicine, vol. 346, No. 11, pp. 793-801 (Mar. 14, 2002).
Noakes, Timothy D., "Lore of Running," Fourth Edition, Human Kinetics, Chapter 2: Oxygen Transport and Running Economy, Chapter 3: Energy Systems and Running Performance, 157 pages (2002).
Rapoport, Benjamin I., "Metabolic Factors Limiting Performance in Marathon Runners," PLoS Computational Biology, vol. 6, Issue 10, 13 pages (Oct. 2010).
Tanaka, H. et al., "Age-predicted maximal heart rate revisited," Journal of the American College of Cardiology, vol. 37, Issue 1, pp. 153-156 (Jan. 2001).
Wang, L. et al., "Time constant of heart rate recovery after low level exercise as a useful measure of cardiovascular fitness," Conf. Proc. IEEE Eng. Med. Biol. Soc., vol. 1, pp. 1799-1802 (2006).
KINprof, 2011, Predictive VO2max tests, Web Video, Retrieved from: https://www.youtube.com/watch?v=_9e3HcYlsm8.
U.S. Appl. No. 15/682,726, 2018-0056123, filed Aug. 31, 2017, Published.
U.S. Appl. No. 15/264,976, 2017-0074897, filed Sep. 14, 2016, Published.
U.S. Appl. No. 14/502,754, 2016-0058371, filed Sep. 30, 2014, Issued.
U.S. Appl. No. 14/493,178, 2015-0087929, filed Sep. 22, 2014, Abandoned.
U.S. Appl. No. 14/145,042, 2015-0088006, filed Dec. 31, 2013, Abandoned.
International Search Report and Written Opinion received for PCT Patent Application No. PCT/US2018/047290, dated Nov. 8, 2018, 14 pages.
Yamaji, et al., "Relationship Between Heart Rate and Relative Oxygen Intake in Male Subjects Aged 10 to 27 Years", J. Human Ergol., 7:29-39, Jan. 27, 1978.
Le, et al., "Sensor-based Training Optimization of a Cyclist Group", Seventh International Conference on Hybrid Intelligent Systems, IEEE 2007, pp. 265-270.
U.S. Appl. No. 15/692,726, U.S. Publication No. 2018-0056123, filed Aug. 31, 2017, Published.
U.S. Appl. No. 15/692,237, U.S. Publication No. 2018-0056129, filed Aug. 31, 2017, Published.
U.S. Appl. No. 15/692,736, U.S. Publication No. 2018-0055375, filed Aug. 31, 2017, Published.
U.S. Appl. No. 15/689,113, U.S. Publication No. 2018-0055439, filed Aug. 29, 2017, Published.
U.S. Appl. No. 15/678,645, U.S. Publication No. 2018-0049694, filed Aug. 16, 2017, Published.
U.S. Appl. No. 15/679,538, U.S. Publication No. 2018-0050235, filed Aug. 17, 2017, Published.
U.S. Appl. No. 15/616,135, U.S. Publication No. 2017-0347885, filed Jun. 7, 2017, Published.
U.S. Appl. No. 15/611,010, U.S. Publication No. 2018-0344217, filed Jun. 1, 2017, Published.
U.S. Appl. No. 14/502,809, U.S. Publication No. 2016-0058333, filed Sep. 30, 2014, Published.
U.S. Appl. No. 15/273,054, U.S. Publication No. 2017-0094450, filed Sep. 22, 2016, Abandoned.
U.S. Appl. No. 15/691,245, U.S. Publication No. 2018-0056128, filed Aug. 30, 2017, Published.
U.S. Appl. No. 14/501,771, U.S. Publication No. 2016-0058370, filed Sep. 30, 2017, Published.
U.S. Appl. No. 15/061,653, U.S. Publication No. 2016-0256058, filed Mar. 4, 2016, Issued.
U.S. Appl. No. 14/501,930, U.S. Publication No. 2016-0058329, filed Sep. 30, 2014, Issued.
U.S. Appl. No. 14/502,827, U.S. Publication No. 2016-0058302, filed Sep. 30, 2014, Issued.
U.S. Appl. No. 14/501,701, U.S. Publication No. 2016-0058332, filed Sep. 30, 2017, Issued.
U.S. Appl. No. 14/501,634, U.S. Publication No. 2016-0058356, filed Sep. 30, 2014, Published.
U.S. Appl. No. 14/502,781, U.S. Publication No. 2016-0058372, filed Sep. 30, 2014, Abandoned.
U.S. Appl. No. 14/502,754, U.S. Publication No. 2016-0058371, filed Sep. 30, 2014, Issued.
U.S. Appl. No. 15/264,976, U.S. Publication No. 2017-0074897, filed Sep. 14, 2016, Published.
U.S. Appl. No. 14/493,178, U.S. Publication No. 2015-0087929, filed Sep. 22, 2014, Abandoned.
U.S. Appl. No. 14/145,042, U.S. Publication No. 2015-0088006, filed Dec. 31, 2013, Abandoned.
U.S. Appl. No. 15/466,397, U.S. Publication No. 2017-0273619, filed Mar. 22, 2017, Published.
U.S. Appl. No. 16/106,763, U.S. Publication No. 2019-0076063, filed Mar. 14, 2019, Published.
Kyle, Chester R., "Reduction of Wind Resistance and Power Output of Racing Cyclists and Runners Travelling in Groups", Ergonomics, vol. 22, No. 4, 1979, pp. 387-397.

* cited by examiner

DETECTING CONTROLLERS IN VEHICLES USING WEARABLE DEVICES

CROSS REFERENCE TO RELATED APPLICATIONS

This application claims priority to U.S. Provisional Pat. App. No. 62/221,903, titled "Detecting Controllers in Vehicles Using Wearable Devices," filed Sep. 22, 2015, which is incorporated by reference in its entirety herein.

FIELD

The present disclosure relates generally to detecting controllers in vehicles and, more particularly, to techniques for determining whether a user is controlling the vehicle or is a passenger in a vehicle using motion data or other information from a wrist-worn device.

BACKGROUND

A wearable device can be worn by controllers or passengers in vehicles. A passenger may wish to enjoy full use of the wearable device, such as by interacting with applications, receiving notifications, or issuing commands by voice or touch. In contrast, a user controlling a vehicle may not want, or may not be able, to safely interact with the wearable device in the same ways that a passenger could. For example, a vehicle controller may not be able to take his or her eyes off the road or hands off the steering wheel to interact with the device.

The wearable device can also include motion sensors to collect data about the wearable device's position and orientation in space and to track changes to the wearable device's position and orientation over time. Because a user can wear the wearable device, the motion data can provide information about the user's movements. For example, when a user is running, the user's arms are typically swinging back and forth over a particular distance and at a particular frequency. If the user wears the wearable device on the user's wrist, the wearable device may be able to infer that the user is running by sensing the way the user's arm moves back and forth.

Because controllers and passengers may prefer or require different uses of the wearable device, it may be advantageous to detect automatically whether a user is controlling a vehicle and adapt its behavior accordingly to better suit the user while the user is controlling a vehicle.

SUMMARY

Embodiments of the present disclosure include a wearable device and techniques for accurately detecting whether a user is controlling a vehicle based on motion data or other information from wearable devices or other mobile devices. The wearable device may be worn on a wrist, such as a watch, and it may include one or more microprocessors, a display, and a variety of sensors, such as a heart rate sensor and one or more motion sensors.

Embodiments of the present disclosure may adapt the behavior of the wearable device according to whether the user is controlling a vehicle (e.g., driving a motor vehicle, steering a bicycle, flying an airplane, navigating a boat or ship, etc.). For example, the wearable device may reduce the type or quantity of notifications that the user receives while the user is controlling a vehicle.

In some embodiments, the motion sensors may include, for example, an accelerometer, a gyroscope, a barometer or altimeter, a magnetometer or compass, etc. The wearable device may also include a motion coprocessor, which may be optimized for low-power, continuous motion sensing and processing.

In some embodiments, the wearable device may be capable of communicating with a companion device. The wearable device may communicate with a companion device wirelessly, e.g., via a Bluetooth connection or similar wireless communication method. The companion device may be a second mobile device, such as a phone, which may include additional sensors. The additional sensors in the companion device may include a Global Positioning System (GPS) sensor, accelerometer, gyroscope, barometer or altimeter, motion coprocessor, etc. The companion device may, for example, communicate location information based on data from the GPS sensor to the wearable device.

In some embodiments, the (first) wearable device may be capable of communicating with other wearable devices. The first wearable device may communicate with other devices wirelessly, e.g., via a Bluetooth connection or similar wireless communication method. In some embodiments, some of the other wearable devices may include different hardware or firmware and may communicate using a common inter-device protocol and implement a given application programming interface (API). The first wearable device may, for example, communicate motion data or other information to the other wearable devices. The first wearable device may also be configured to receive information in kind from the other wearable devices.

In one aspect, the present disclosure relates to a method, including receiving, by a wearable device, motion information from a motion sensor of the wearable device, determining, by the wearable device using the motion information, that a vehicle is turning, and determining, by the wearable device using the motion information when the vehicle is turning, that a user of the wearable device is controlling the vehicle. In some embodiments, this aspect further includes adjusting the operation of the wearable device while the user is determined to be controlling the vehicle, including wherein adjusting the operation of the wearable device comprises reducing an amount of notifications routed to a display of the wearable device. In some embodiments, adjusting the operation of the wearable device may include the wearable device ignoring a recognized gesture.

In some embodiments, this aspect includes wherein determining that a vehicle is turning includes determining an angular velocity of the wearable device, estimating the angular velocity of the wearable device attributable to the vehicle, and determining that the vehicle is turning when the estimated angular velocity exceeds a threshold value of angular velocity.

In some embodiments, this aspect includes determining that a user of the wearable device is controlling the vehicle, wherein determining that a user of the wearable device is controlling the vehicle includes receiving, by a wearable device, motion information from a companion device, estimating an angular velocity of the wearable device not attributable to the motion of vehicle based on the motion information from the wearable device and the motion information from the companion device, and estimating the likelihood that the user is controlling the vehicle based on the estimated angular velocity of the wearable device not attributable to the motion of the vehicle.

In some embodiments, this aspect includes estimating a direction of gravity relative to the wearable device based on the motion information from the wearable device, determining a turning axis of the vehicle based on the estimated direction of gravity and the motion information from the wearable device, and estimating an angular velocity of the vehicle, wherein the angular velocity of the vehicle is used to determine that the vehicle is turning. Estimating a direction of gravity relative to the wearable device may be not performed when an angular velocity of the wearable device exceeds a first threshold.

In some embodiments, this aspect further includes receiving, by a wearable device, motion information from a companion device, estimating a direction of gravity relative to the companion device based on the motion information from the companion device, determining a turning axis of the vehicle based on the estimated direction of gravity and the motion information from the wearable device, and estimating an angular velocity of the vehicle, wherein the angular velocity of the vehicle is used to determine that the vehicle is turning. These embodiments may further include determining the direction of gravity relative to the wearable device based at least in part on the direction of gravity relative to the companion device.

In some embodiments, this aspect further includes determining that the user of the wearable device is controlling the vehicle wherein the determination is based at least in part on one or more of a noise level of the motion information, vehicle information received via a vehicle network bus, a sensor detecting a clenched hand of the user, or an angle of a limb of the user on which the wearable device is worn.

In a further aspect, the present disclosure relates to a wearable device, including a motion sensor for obtaining motion information of a user of the wearable device and a processor communicatively coupled to the motion sensor, wherein the processor is configured to receive motion information from the motion sensor, determine, using the motion information, that a vehicle is turning, and determine, using the motion information when the vehicle is turning, that the user is controlling the vehicle.

In some embodiments, this aspect further includes the processor further configured to adjust the operation of the wearable device while the user is determined to be controlling the vehicle. In at least some embodiments, adjusting the operation of the wearable device includes reducing an amount of notifications routed to a display of the wearable device or ignoring a recognized gesture.

In some embodiments of this aspect, determining that a vehicle is turning includes determining an angular velocity of the wearable device, estimating the angular velocity of the wearable device attributable to the vehicle, and determining that the vehicle is turning when the estimated angular velocity exceeds a threshold value of angular velocity.

In some embodiments of this aspect, the processor is further communicatively coupled to a companion device and the processor is further configured to receive motion information from the companion device, estimate an angular velocity of the wearable device not attributable to the motion of vehicle based on the motion information from the wearable device and the motion information from the companion device, and estimate the likelihood that the user is controlling the vehicle based on the estimated angular velocity of the wearable device not attributable to the motion of the vehicle, wherein the estimated likelihood that the user is controlling the vehicle is used to determine that the user of the wearable device is controlling the vehicle.

In some embodiments of this aspect, the processor is further configured to estimate a direction of gravity relative to the wearable device based on the motion information from the wearable device, determine a turning axis of the vehicle based on the estimated direction of gravity and the motion information from the wearable device, and estimate an angular velocity of the vehicle, wherein the angular velocity of the vehicle is used to determine that the vehicle is turning. In at least some of these embodiments, estimating a direction of gravity relative to the wearable device is not performed when an angular velocity of the wearable device exceeds a first threshold.

In some embodiments of this aspect, the processor is communicatively coupled to a companion device and the processor is further configured to receive motion information from the companion device, estimate a direction of gravity relative to the companion device based on the motion information from the companion device, determine a turning axis of the vehicle based on the estimated direction of gravity and the motion information from the wearable device, and estimate an angular velocity of the vehicle, wherein the angular velocity of the vehicle is used to determine that the vehicle is turning.

Other features and advantages will become apparent from the following detailed description and drawings.

BRIEF DESCRIPTION OF THE DRAWINGS

In order to facilitate a fuller understanding of the present disclosure, reference is now made to the accompanying drawings, in which like elements are referenced with like numerals. These drawings should not be construed as limiting the present disclosure, but are intended to be illustrative only.

DESCRIPTION

The present disclosure describes a wearable device that may be configured to detect whether a user is controlling a vehicle. The wearable device may adapt its behavior according to whether the user is controlling a vehicle.

Figure 1:
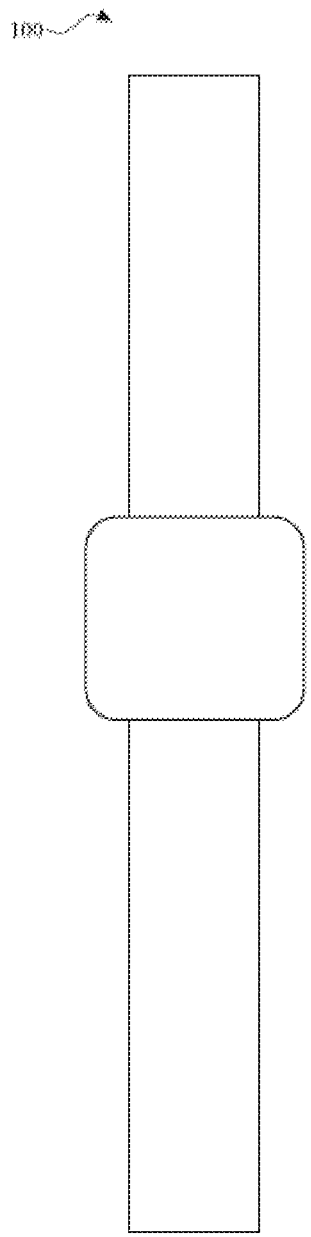
FIG. 1 shows a wearable device in accordance with an embodiment of the present disclosure.

FIG. 1 shows an example of a wearable device 100 in accordance with an embodiment of the present disclosure. In some embodiments, the wearable device 100 may be any suitable wearable device, such as a watch configured to be worn around an individual's wrist. As described in more detail below, the wearable device 100 may be calibrated according to physical attributes of the individual and physical activity by the individual user who is wearing the wearable device 100, including, for example, activity participation statistics.

Figure 2:
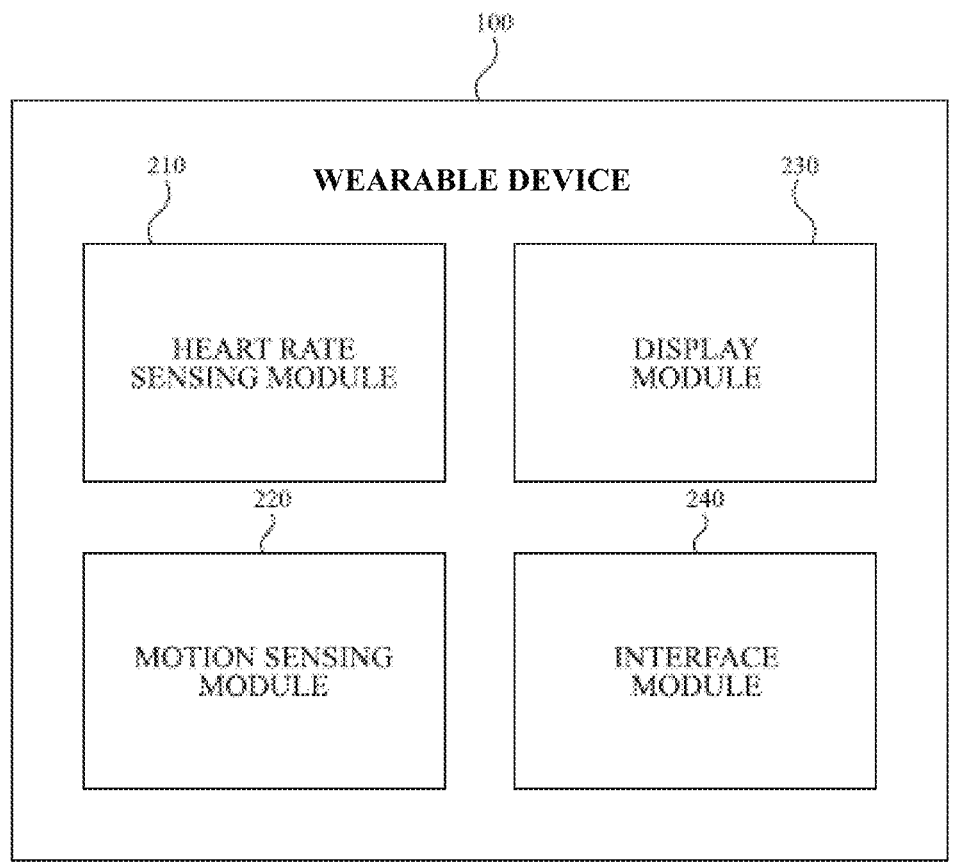
FIG. 2 depicts a block diagram of a wearable device in accordance with an embodiment of the present disclosure.

FIG. 2 depicts a block diagram of example components that may be found within the wearable device 100 in accordance with an embodiment of the present disclosure. These components may include a heart rate sensing module 210, a motion sensing module 220, a display module 230, and an interface module 240.

The heart rate sensing module 210 may include or may be in communication with a heart rate sensor as previously described. The wearable device 100 can measure an individual's current heart rate from the heart rate sensor. The heart rate sensor may also be configured to determine a confidence level indicating a relative likelihood of an accuracy of a given heart rate measurement. In other embodiments, a traditional heart rate monitor may be used and may communicate with the wearable device 100 through a near field communication method (e.g., Bluetooth).

The wearable device 100 may also include the motion sensing module 220. The motion sensing module 220 may include one or more motion sensors, such as an accelerometer or a gyroscope. In some embodiments, the accelerometer may be a three-axis, microelectromechanical system (MEMS) accelerometer, and the gyroscope may be a three-axis MEMS gyroscope. A microprocessor (not shown) or motion coprocessor (not shown) of the wearable device 100 may receive motion information from the motion sensors of the motion sensing module 220 to track acceleration, rotation, position, or orientation information of the wearable device 100 in six degrees of freedom through three-dimensional space.

In some embodiments, the motion sensing module 220 may include other types of sensors in addition to accelerometers and gyroscopes. For example, the motion sensing module 220 may include an altimeter or barometer, or other types of location sensors, such as a GPS sensor.

The wearable device 100 may also include the display module 230. Display module 230 may be a screen, such as a crystalline (e.g., sapphire) or glass touchscreen, configured to provide output to the user as well as receive input from the user via touch. For example, display 230 may be configured to display a current heart rate or a daily average energy expenditure. Display module 230 may receive input from the user to select, for example, which information should be displayed, or whether the user is beginning a physical activity (e.g., starting a session) or ending a physical activity (e.g., ending a session), such as a running session or a cycling session. In some embodiments, the wearable device 100 may present output to the user in other ways, such as by producing sound with a speaker (not shown), and the wearable device 100 may receive input from the user in other ways, such as by receiving voice commands via a microphone (not shown).

In some embodiments, the wearable device 100 may communicate with external devices via interface module 240, including a configuration to present output to a user or receive input from a user. Interface module 240 may be a wireless interface. The wireless interface may be a standard Bluetooth (IEEE 802.15) interface, such as Bluetooth v4.0, also known as "Bluetooth low energy." In other embodiments, the interface may operate according to a cellphone network protocol such as LTE or a Wi-Fi (IEEE 802.11) protocol. In other embodiments, interface module 240 may include wired interfaces, such as a headphone jack or bus connector (e.g., Lightning, Thunderbolt, USB, etc.).

The wearable device 100 may be configured to communicate with a companion device 300 (FIG. 3), such as a smartphone, as described in more detail herein. In some embodiments, the wearable device 100 may be configured to communicate with other external devices, such as a notebook or desktop computer, tablet, headphones, Bluetooth headset, etc.

The modules described above are examples, and embodiments of the wearable device 100 may include other modules not shown. For example, the wearable device 100 may include one or more microprocessors (not shown) for processing heart rate data, motion data, other information in the wearable device 100, or executing instructions for firmware or apps stored in a non-transitory processor-readable medium such as a memory module (not shown). Additionally, some embodiments of the wearable device 100 may include a rechargeable battery (e.g., a lithium-ion battery), a microphone or a microphone array, one or more cameras, one or more speakers, a watchband, a crystalline (e.g., sapphire) or glass-covered scratch-resistant display, water-resistant casing or coating, etc.

Figure 3:
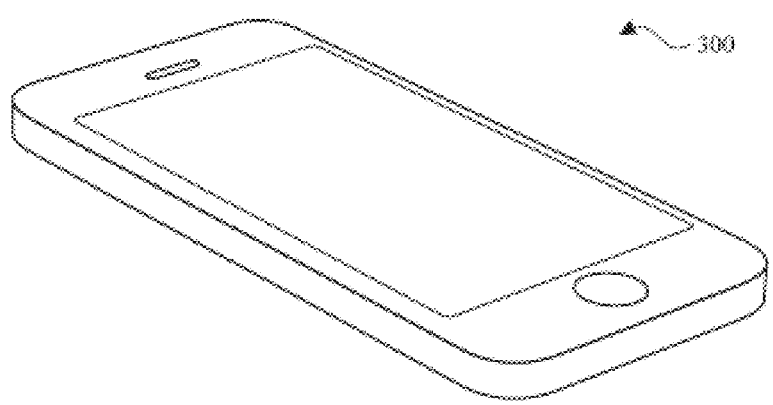
FIG. 3 shows a companion device in accordance with an embodiment of the present disclosure.

FIG. 3 shows an example of a companion device 300 in accordance with an embodiment of the present disclosure. The wearable device 100 may be configured to communicate with the companion device 300 via a wired or wireless communication channel (e.g., Bluetooth, Wi-Fi, etc.). In some embodiments, the companion device 300 may be a smartphone, tablet computer, or similar portable computing device. The companion device 300 may be carried by the user, stored in the user's pocket, strapped to the user's arm with an armband or similar device, placed in a mounting device, or otherwise positioned within communicable range of the wearable device 100.

The companion device 300 may include a variety of sensors, such as location and motion sensors (not shown). When the companion device 300 may be optionally available for communication with the wearable device 100, the wearable device 100 may receive additional data from the companion device 300 to improve or supplement its calibration or calorimetry processes. For example, in some embodiments, the wearable device 100 may not include a GPS sensor as opposed to an alternative embodiment in which the wearable device 100 may include a GPS sensor. In the case where the wearable device 100 may not include a GPS sensor, a GPS sensor of the companion device 300 may collect GPS location information, and the wearable device 100 may receive the GPS location information via interface module 240 (FIG. 2) from the companion device 300.

In another example, the wearable device 100 may not include an altimeter or barometer, as opposed to an alternative embodiment in which the wearable device 100 may include an altimeter or barometer. In the case where the wearable device 100 may not include an altimeter or barometer, an altimeter or barometer of the companion device 300 may collect altitude or relative altitude information, and the wearable device 100 may receive the altitude or relative altitude information via interface module 240 (FIG. 2) from the companion device 300.

In another example, the wearable device 100 may receive motion data from the companion device 300. The wearable device 100 may compare the motion data from the companion device 300 with motion data from the motion sensing module 220 of the wearable device 100. Motion data such as accelerometer or gyroscope data may be filtered (e.g. by a high-pass, low-pass, band-pass, or band-stop filter) in order to improve the quality of motion data. For example, a low-pass filter may be used to remove vibrations such as road noise.

The wearable device may use motion data to predict a user's activity. Examples of activities may include, but are not limited to, walking, running, cycling, swimming, etc. The wearable device may also be able to predict or otherwise detect when a user is sedentary (e.g., sleeping, sitting, standing still, driving or otherwise controlling a vehicle, etc.) The wearable device may use a variety of motion data, including, in some embodiments, motion data from a companion device.

The wearable device may use a variety of heuristics, algorithms, or other techniques to predict the user's activity. The wearable device may also estimate a confidence level (e.g., percentage likelihood, degree of accuracy, etc.) associated with a particular prediction (e.g., 90% likelihood that the user is running) or predictions (e.g., 60% likelihood that the user is running and 40% likelihood that the user is walking).

Figure 4:
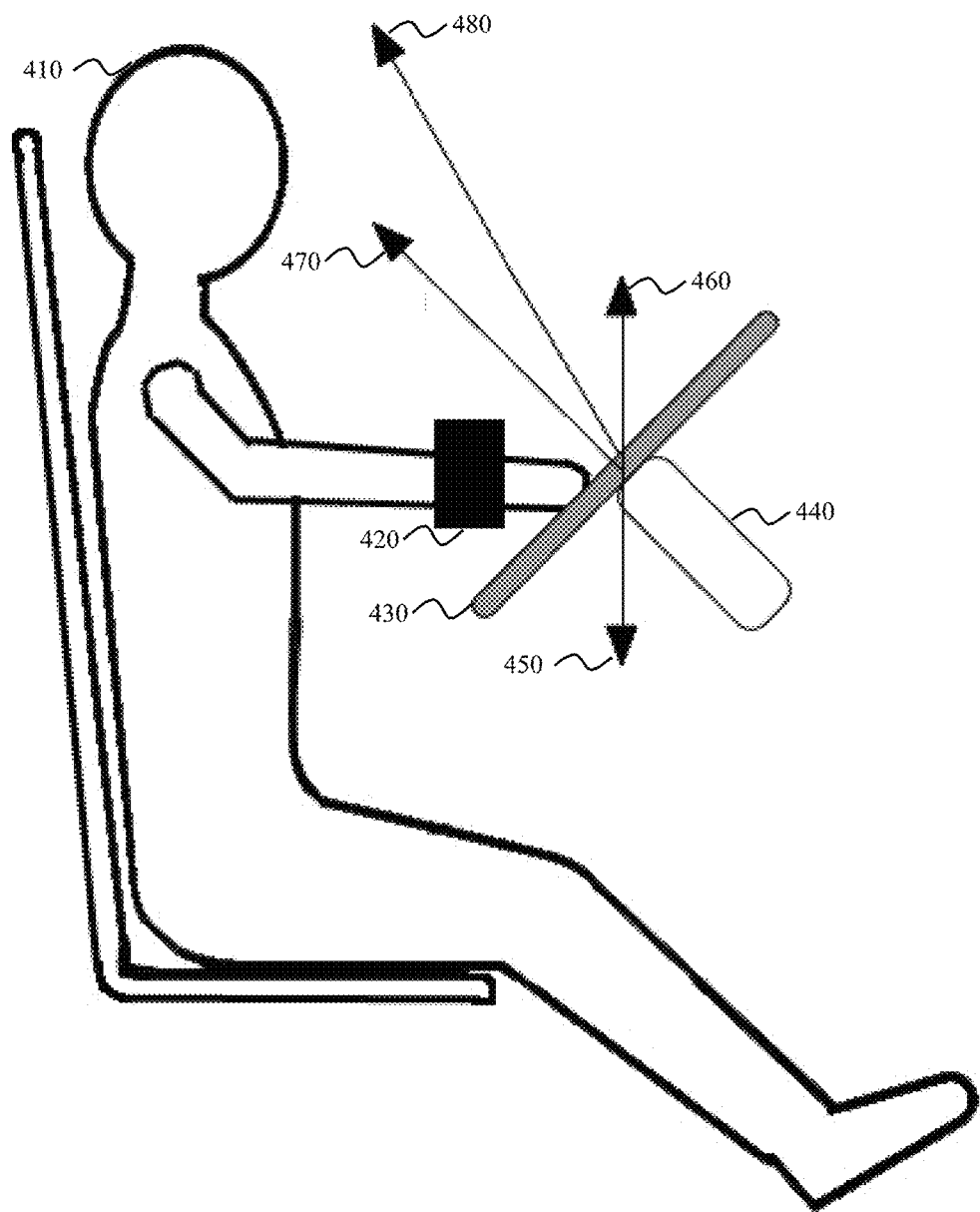
FIG. 4 shows a schematic representation of a user with a wearable device controlling a vehicle in accordance with an embodiment of the present disclosure.

FIG. 4 shows a schematic representation of a user controlling a vehicle with a wearable device in accordance with an embodiment of the present disclosure. In the example of FIG. 4, a user 410 is wearing a wearable device 420 (e.g., the wearable device 100) on the user's wrist. The user may be holding a steering wheel 430 of the vehicle, which may be coupled to a steering column 440 or a similar component of the vehicle. In some embodiments, the wearable device 420 may be worn on other portions of the user's body, such as the arm, finger, leg, or foot, so long as the portion of the user's body experiences motion related to controlling the vehicle.

FIG. 4 also depicts a set of vectors 450, 460, 470, and 480. These vectors may be measured directly or estimated from motion data. Vector 450 represents the direction of gravity. In the example of FIG. 4, the vehicle is on relatively level terrain (relatively little or no pitch), and the direction of gravity acting on the vehicle is shown as "down," approximately perpendicular to the road or other terrain.

Vector 460 is an "axial vector" or "pseudovector" representing the angular velocity of the vehicle when the vehicle is turning ("$\omega_{vehicle}$"). In the example of FIG. 4, in which the vehicle is on approximately level terrain, the axis of rotation of the vehicle may be correlated with the direction of gravity vector 450.

Vector 470 is an axial vector representing the angular velocity of the steering wheel when the steering wheel is turning ("$\omega_{steering}$"). In the example of FIG. 4, the axis of rotation of the steering wheel may be correlated with the angle of the steering column 440. In some embodiments, the angle of the steering column 440 in a vehicle may be adjustable.

Vector 480 is an axial vector representing the angular velocity of the wearable device 420 ($\omega_{wearable}$). In the example of FIG. 4, the user 410 may steer the vehicle using steering wheel 430 with an angular velocity $\omega_{steering}$, causing the vehicle to turn with an angular velocity $\omega_{vehicle}$. The wearable device 420 may rotate during the turn as well with an angular velocity $\omega_{wearable}$. Part of the rotation of the wearable device 420 may be attributable to turning the steering wheel, with a component axis similar to the steering vector 470, and another part of the rotation of the wearable device 420 may be attributable to the vehicle turning, with a component axis similar to the vector 460. Thus, the angular velocity of the wearable device 120 may be estimated to be (approximately) equal to the sum of the angular velocities of the steering wheel 430 and the vehicle, as shown in Equation 1:

$$\omega_{wearable} = \omega_{steering} + \omega_{vehicle} \qquad (\text{Eq. 1})$$

Figure 5:
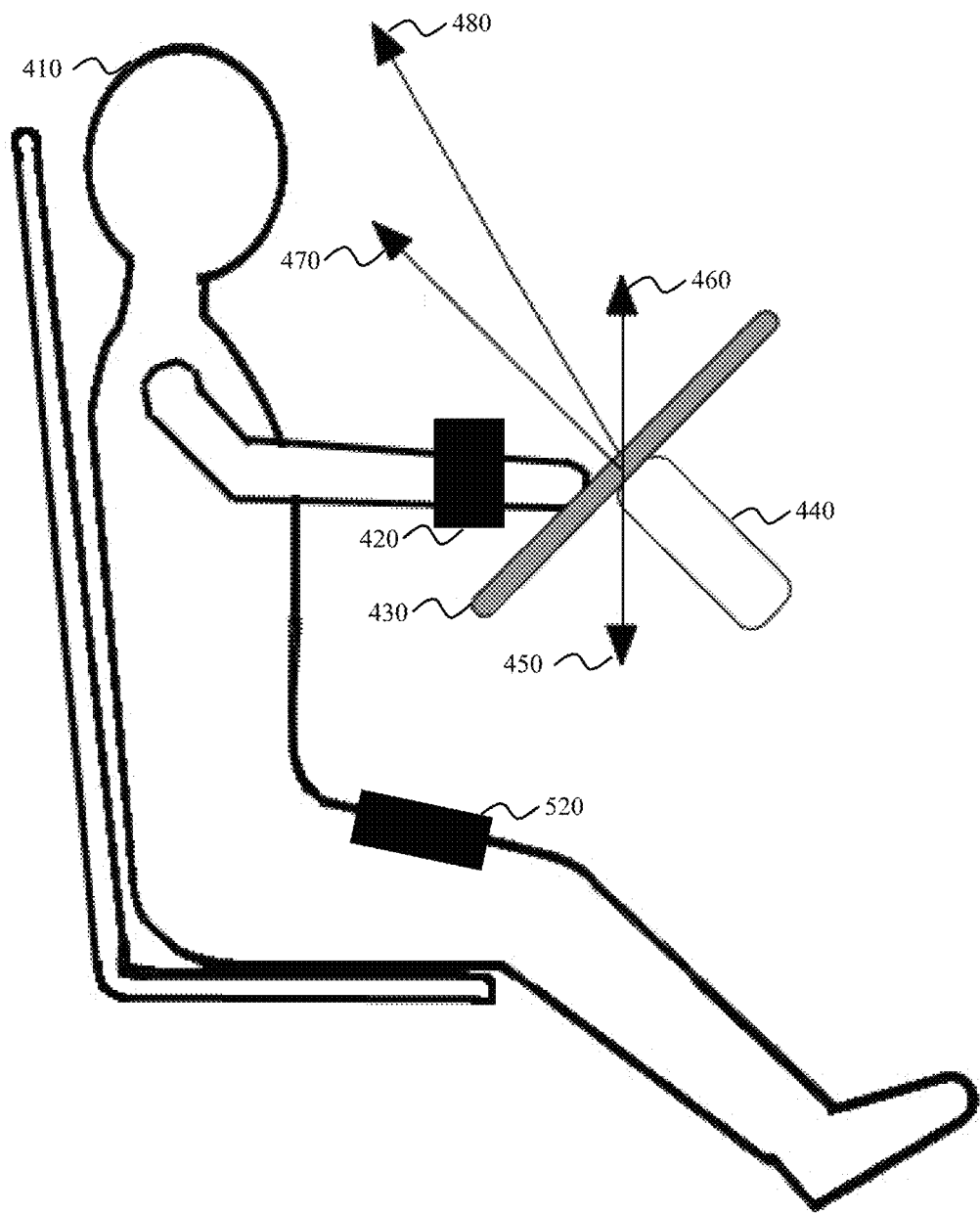
FIG. 5 shows a schematic representation of a user with a wearable device and a companion device, controlling a vehicle in accordance with an embodiment of the present disclosure.

FIG. 5 shows a schematic representation of a user controlling a vehicle with a wearable device and a companion device in accordance with an embodiment of the present disclosure. In the example of FIG. 5, like the example of FIG. 4, the user 410 is controlling a vehicle with steering wheel 430 coupled to steering column 440. Vectors 450 represents the direction of gravity, vector 460 represents the turning axis of the vehicle, vector 470 represents the turning axis of the steering wheel 430, and vector 480 represents the turning axis of the wearable device 420, which may be approximately equal to the sum of the vectors 470 and 480.

In FIG. 5, the user 410 may also have a companion device 520 (e.g., the companion device 300) in the vehicle. In the example of FIG. 5, the companion device 520 may be in a pocket of the user 410. In some embodiments, companion device 520 may be worn on, carried in clothing covering, or clipped to a portion of the user's body that does not experience motion related to controlling the vehicle. The companion device 520 will experience the same gravity as the vehicle (e.g., vector 450) and may rotate around the same turning axis of the vehicle (e.g., vector 460). However, while the companion device 520 is in a pocket of the user 410, it would not experience rotation around the turning axis of the steering wheel (e.g., vector 470). Thus, the angular velocity of the companion device 520 ($\omega_{companion}$) may be estimated to be (approximately) equal to the angular velocity of the vehicle, as shown in Equation 2:

$$\omega_{companion} = \omega_{vehicle} \qquad (\text{Eq. 2})$$

Because $\omega_{vehicle}$ may be approximately equal to $\omega_{companion}$, $\omega_{wearable}$ may be estimated to be (approximately) equal to the sum of the angular velocities of the steering wheel 430 and the companion device 520, as shown in Equation 3:

$$\omega_{wearable} = \omega_{steering} + \omega_{companion} \qquad (\text{Eq. 3})$$

The companion device may communicate either a vector estimate of gravity or $\omega_{companion}$ to the wearable device.

Figure 6A:
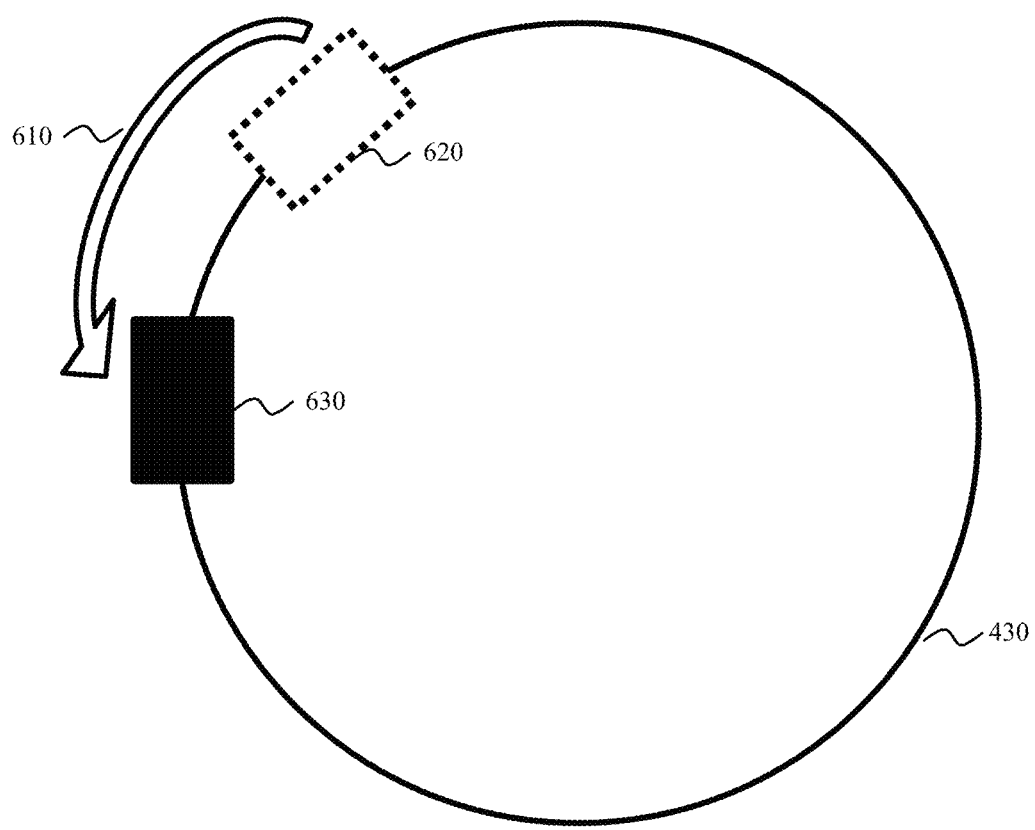
FIG. 6A depicts a schematic representation of a wearable device moving while a user is controlling a vehicle in accordance with an embodiment of the present disclosure.

FIG. 6A depicts a schematic representation of a wearable device moving while a user is controlling a vehicle in accordance with an embodiment of the present disclosure. In the example of FIG. 6A, the user (not shown) is turning the steering wheel 430 in the direction indicated by the counterclockwise arrow 610. The user's hand may move from an initial position 620 (e.g., the "10 o'clock" position) to a subsequent position 630 (e.g., the "9 o'clock" position). Because the user is wearing a wearable device (e.g., the wearable device 420 (FIGS. 4 and 5)), the wearable device also moves from the initial position 620 to the subsequent position 630 relative to the steering wheel 430. As shown in FIG. 6A, the user's wearable device may rotate from an initial orientation (as in initial position 620) to a subsequent orientation (as in subsequent position 630).

Figure 6B:
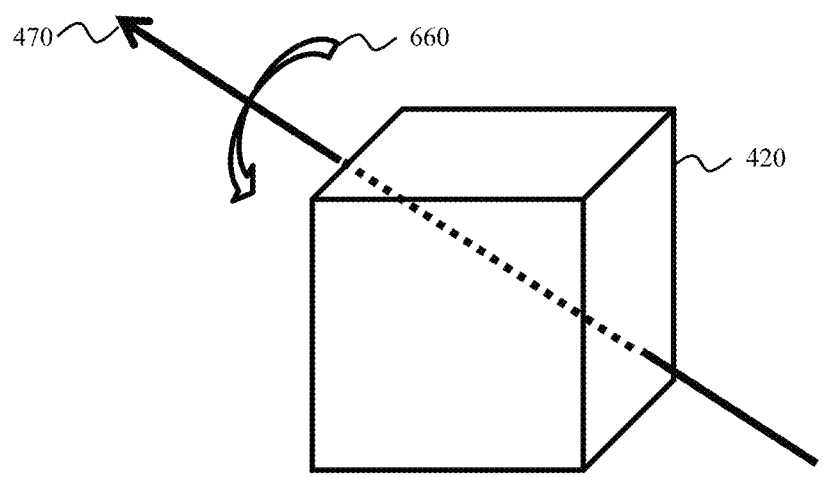
FIG. 6B depicts a schematic representation of movement of a wearable device while a user is controlling a vehicle in accordance with an embodiment of the present disclosure.

FIG. 6B depicts a schematic representation of movement of a wearable device while a user is controlling a vehicle in accordance with an embodiment of the present disclosure. In FIG. 6B, the wearable device 420 is depicted schematically as an object in three-dimensional space. Vector 470 (for $\omega_{steering}$) is shown as the turning axis for the wearable device. The rotational arrow 660 indicates that the wearable device 420 may rotate—or rotate in part—according to the vector 470 as the steering wheel turns as indicated in FIG. 6A.

Figure 7A:
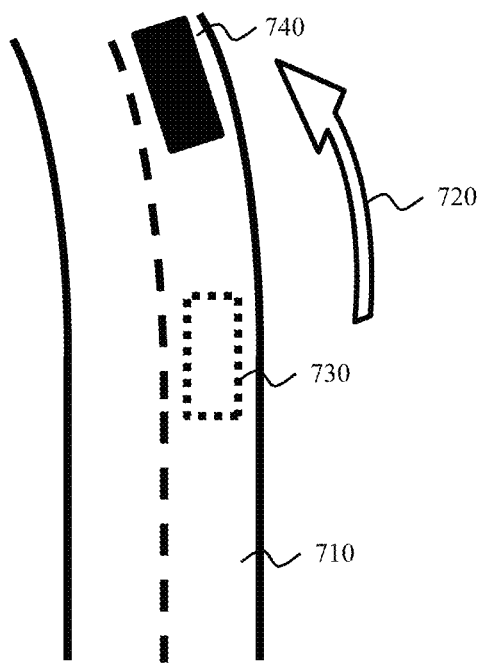
FIG. 7A shows a schematic representation of a wearable device moving while a user is controlling a vehicle in accordance with an embodiment of the present disclosure.

FIG. 7A shows a schematic representation of a wearable device moving while a user is controlling a vehicle in accordance with an embodiment of the present disclosure. In the example of FIG. 7A, the user (not shown) is either controlling a vehicle or riding in a vehicle on a road 710 or other surface. The vehicle turns in the direction indicated by the counterclockwise arrow 720. The vehicle may move from an initial position 730 to a subsequent position 740. Because the user is wearing a wearable device (e.g., the wearable device 420 (FIGS. 4 and 5)), the wearable device also moves from the initial position 730 to the subsequent position 740 relative to the vehicle. Additionally, the user's wearable device may rotate from an initial orientation (as in initial position 730) to a subsequent orientation (as in subsequent position 740).

Figure 7B:
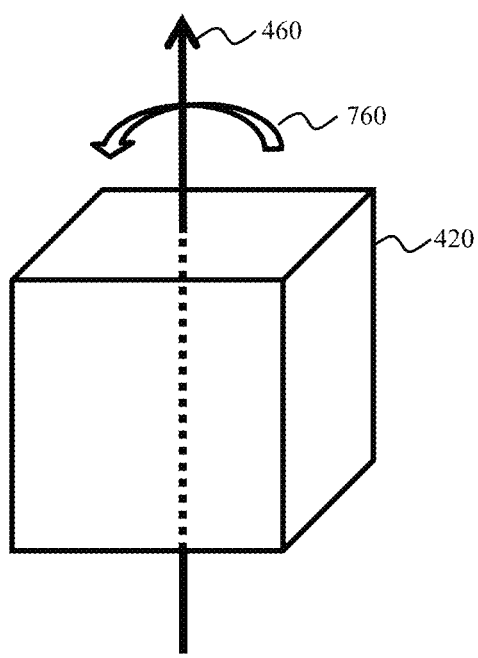
FIG. 7B shows a schematic representation of movement of a wearable device while a user is controlling a vehicle in accordance with an embodiment of the present disclosure.

FIG. 7B shows a schematic representation of movement of a wearable device while a user is controlling a vehicle in accordance with an embodiment of the present disclosure. In FIG. 7B, the wearable device 420 is depicted schematically as an object in three-dimensional space. Vector 460 (for $\omega_{vehicle}$) is shown as the turning axis for the wearable device. The rotational arrow 760 indicates that the wearable device 420 may rotate—or rotate in part—according to the vector 470 as the vehicle turns as indicated in FIG. 7A. In some embodiments, in which the user also has a companion device (e.g., the companion device 520 (FIG. 5), not shown), the companion device may rotate according to the vector 470 and the rotational arrow 760.

Figure 8:
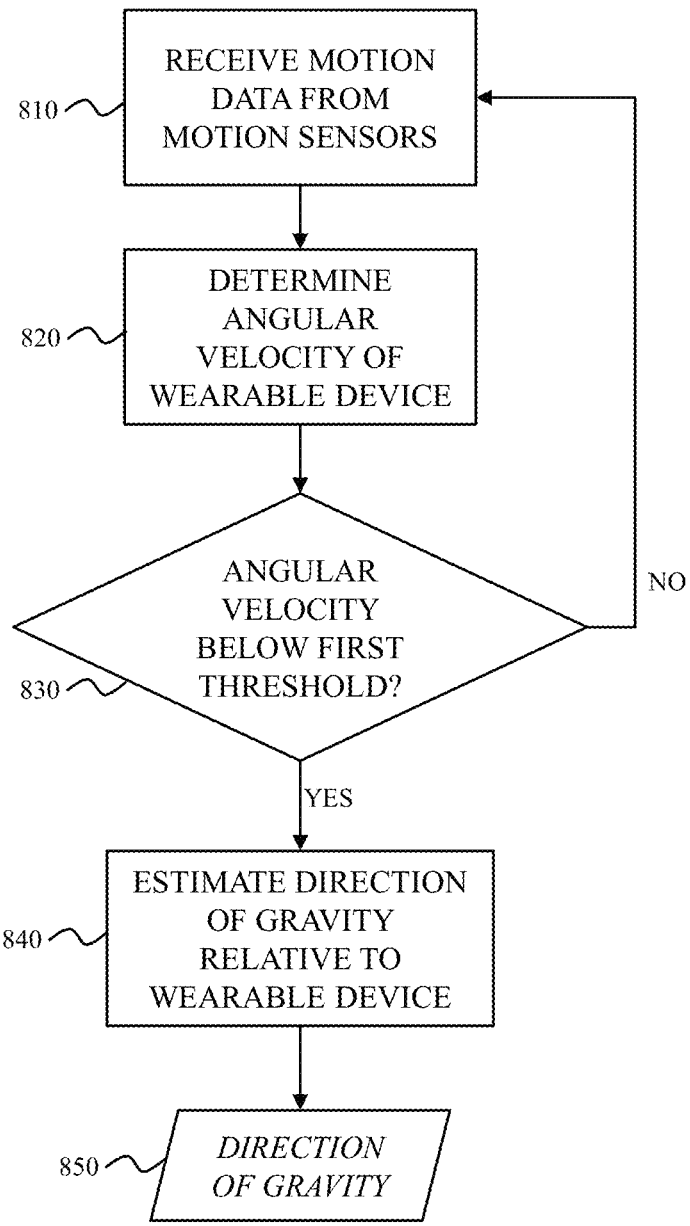
FIG. 8 shows a method for determining a direction of gravity in accordance with an embodiment of the present disclosure.
Figure 9:
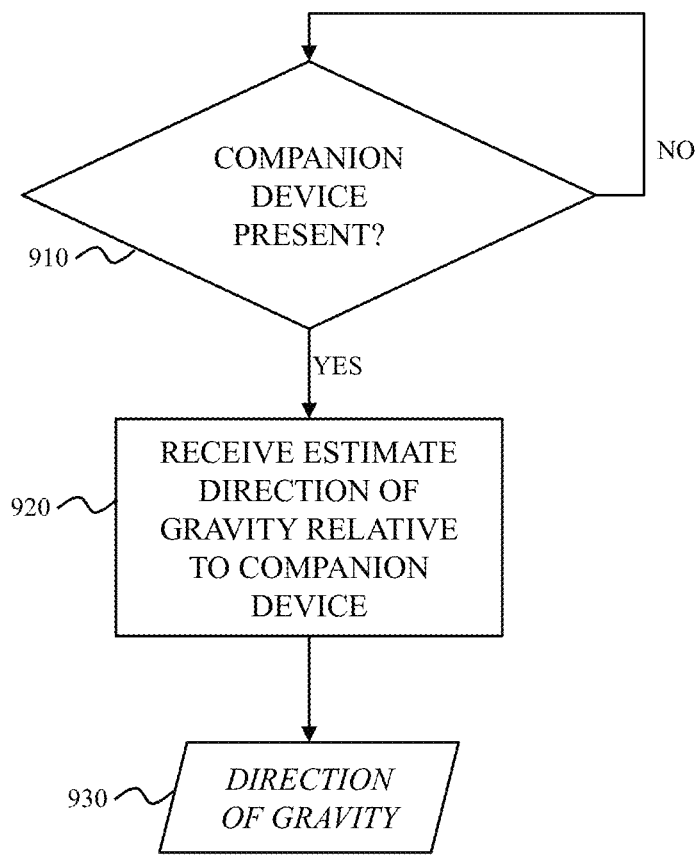
FIG. 9 shows a method for determining a direction of gravity in accordance with an embodiment of the present disclosure.
Figure 10:
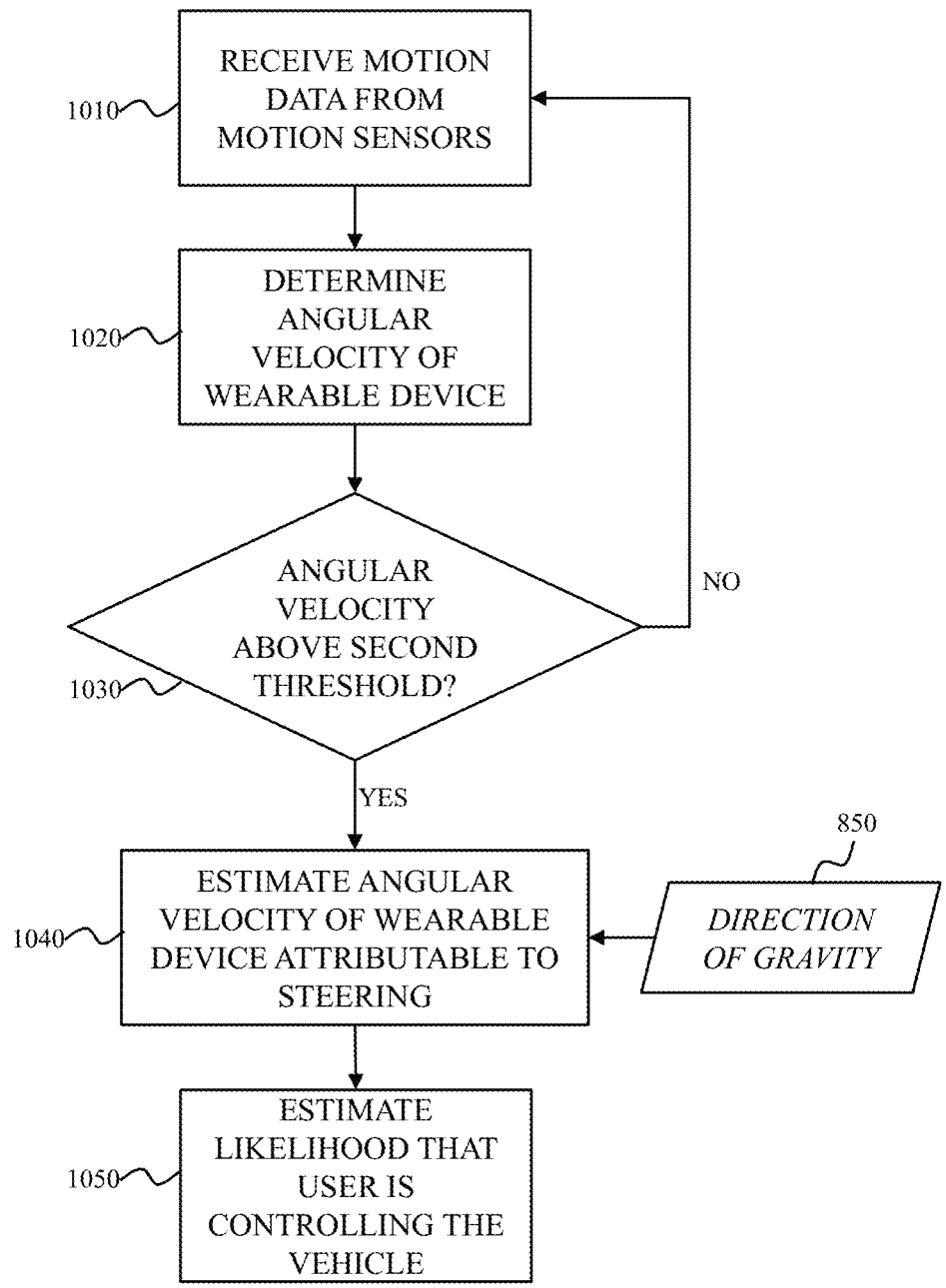
FIG. 10 shows a method for detecting that a user is controlling a vehicle in accordance with an embodiment of the present disclosure.

FIGS. 8-10 depict methods for estimating the likelihood that a user is controlling a vehicle based on motion information from a wearable device or a combination of motion information from a wearable device and a companion device. For example, in some embodiments described below, the wearable device can estimate the turning axis of the vehicle based on the direction of gravity when the vehicle is not turning, because the turning axis of the vehicle may be approximately parallel to the direction of gravity. When the vehicle is turning, the wearable device can estimate whether it is turning solely due to the turning of the vehicle (e.g., when the user is a passenger), or if it is turning due to a combination of turning with the vehicle and turning with the steering wheel (e.g., when the user is controlling the vehicle).

FIG. 8 shows a method for determining a direction of gravity in accordance with an embodiment of the present disclosure. Gravity determination method 800 may begin at block 810.

At block 810, motion data may be received from motion sensors on a wearable device (e.g., wearable device 100) of a user. In some embodiments, motion data may include three-dimensional rotational information from one or more sensors such as a gyroscope. In some embodiments, motion data may be filtered such as by a low-pass filter to remove unwanted noise from the signal (e.g., road noise.)

At block 820, the angular velocity of the wearable device ($\omega_{wearable}$) may be determined. For example, when the vehicle is not turning, $\omega_{vehicle}$ may be approximately 0, and $\omega_{steering}$ may be approximately 0. Consequently, $\omega_{wearable}$ may also be approximately 0 (e.g., in accordance with Equation 1 described above). If the vehicle is turning, $\omega_{vehicle}$ will be greater than 0. For example, $\omega_{vehicle}$ may be greater than approximately 0.2 radians per second, or 0.5 radians per second, or 1.0 radians per second.

At block 830, the gravity determination method 800 may determine whether the angular velocity of the wearable device determined at block 820 is below a first threshold. For example, the first threshold may be approximately 0.05 radians per second, 0.2 radians per second, or 0.5 radians per second, etc. If the angular velocity exceeds the first threshold (e.g., when the vehicle is turning), the gravity determination method 800 may return to block 810. In some embodiments, the gravity determination method 800 may pause or wait for a period of time (e.g., 1 second, 5 seconds, 1 minute, etc.) before proceeding at block 810.

If the angular velocity is below the first threshold (e.g., when the vehicle is not turning), the gravity determination method 800 may proceed to block 840. In some embodiments, at block 830 the wearable device also determines if the magnitude of forces acting on the wearable device are approximately equal to the normal force of gravity (1 g) before proceeding to block 840. If the magnitude is not approximately the normal magnitude, the gravity determination method 800 may also return to block 810.

At block 840, the direction of gravity 850 relative to the wearable device may be estimated. For example, in some embodiments, when $\omega_{wearable}$ is approximately zero, accelerometers within the wearable device may provide data about the direction of forces acting on the wearable device, which may be attributable primarily to gravity. In some embodiments, the gravity determination method 800 may also determine whether the vehicle is accelerating (e.g., speeding up or slowing down) or traveling at an approximately constant velocity so as to further improve the estimate of the direction of gravity 850.

In some embodiments, gravity determination method 800 may end after outputting the estimated direction of gravity 850. In other embodiments, the gravity determination method 800 may return to block 810 (not shown) to refine or otherwise repeat the method of estimating the direction of gravity 850 relative to the wearable device.

FIG. 9 shows a method for determining a direction of gravity in accordance with an embodiment of the present disclosure. Gravity determination method 900 may begin at block 910.

At block 910, gravity determination method 900 may periodically or continuously check for the presence of a companion device (e.g., companion device 300). For example, in some embodiments, a wearable device may determine whether a connection (e.g., Bluetooth, IEEE 802.11 Wi-Fi, or other wireless or wired communication channel) has been established or may be established with a companion device. If a companion device is present, gravity determination method 900 may proceed to block 920.

At block 920, the direction of gravity relative to the companion device may be estimated. In some embodiments, in contrast to gravity determination method 800, it may not be necessary to check whether the angular velocity of the companion device is below a first threshold because most or all of rotation of the angular velocity of the companion device may be orthogonal to the direction of gravity (the companion device may not rotate about an axis attributable in part to the steering wheel regardless of whether the user is controlling the vehicle because the companion device may be in the user's pocket or in an otherwise relatively stationary position within the vehicle).

At block 930, the direction of gravity relative to the companion device may be outputted. In some embodiments, the direction of gravity relative to the companion device may be combined or otherwise compared with the direction of gravity relative to the wearable device. In some embodiments, the companion device may further determine a rotation rate around the direction of gravity relative to the companion device ($\omega_{companion}$) and output the rotation rate instead of or in addition to the direction of gravity relative to the companion device.

In some embodiments, gravity determination method 900 may end after outputting the estimated direction of gravity 850. In other embodiments, the gravity determination method 900 may return to block 910 (not shown) to refine or otherwise repeat the method of estimating the direction of gravity 850 relative to the wearable device FIG. 10 shows a method for detecting that a user is controlling a vehicle in accordance with an embodiment of the present disclosure. Controller detection method 1000 may begin at block 1010.

At block 1010, motion data may be received from motion sensors on a wearable device (e.g., wearable device 100) of a user. In some embodiments, motion data may include three-dimensional rotational information from one or more sensors such as a gyroscope.

At block 1020, the angular velocity of the wearable device ($\omega_{wearable}$) may be determined. For example, when the vehicle is not turning, $\omega_{vehicle}$ may be approximately 0, and $\omega_{steering}$ may be approximately 0. Consequently, $\omega_{wearable}$ may also be approximately 0 (e.g., in accordance with Equation 1 described above). If the vehicle is turning, $\omega_{vehicle}$ will be greater than 0. For example, $\omega_{vehicle}$ may be greater than approximately 0.2 radians per second, or 0.5 radians per second, or 1.0 radians per second. In some embodiments, $\omega_{vehicle}$ may be determined by reference to $\omega_{companion}$ received from a companion device.

Also at block 1020, when the magnitude of $\omega_{vehicle}$ is near zero but $\omega_{wearable}$ is not near zero, $\omega_{wearable}$ may be used to estimate the unit vector of the steering wheel (i.e., the axis of rotation of the steering wheel), as the axis of rotation of the wearable device would coincide with the unit vector of the steering wheel. This situation might occur when the wearer slides their hand along the steering wheel without turning it, or when the wearer turns the steering wheel but the vehicle's actual turning lags behind the steering wheel.

At block 1030, the controller detection method 1000 may determine whether the angular velocity of the wearable device determined at block 1020 is above a second threshold. For example, the second threshold may be approximately 0.05 radians per second, 0.2 radians per second, or 0.5 radians per second, etc. If the angular velocity does not exceed the second threshold (e.g., when the vehicle is not turning), the controller detection method 1000 may return to block 1010. In some embodiments, the controller detection method 1000 may pause or wait for a period of time (e.g., 1 second, 5 seconds, 1 minute, etc.) before proceeding at block 1010.

If the angular velocity is above the second threshold (e.g., when the vehicle is turning), the controller detection method 1000 may proceed to block 1040.

At block 1040, the angular velocity of the wearable device attributable to steering may be estimated. In some embodiments, the direction of gravity 850 may be used to determine the turning axis of the vehicle. By subtracting the rotation due to the turning of the vehicle from the angular velocity of the wearable device, the remainder may be the rotation attributable to steering. This calculation may be derived from Equation 1 described above, as shown in Equation 3:

$$\omega_{steering} = \omega_{wearable} - \omega_{vehicle} \qquad (Eq. 3)$$

For example, if the user is not controlling the vehicle, the user's wearable device will rotate due to the turning of the vehicle, but it may not rotate due to the turning of the steering wheel. Thus, $\omega_{steering}$ may be approximately 0 for a user who is a passenger rather than a controller. If the user is controlling the vehicle, the user's wearable device may rotate due to both the turning of the vehicle and the turning of the steering wheel, and $\omega_{steering}$ may be greater than 0 (e.g., greater than approximately 0.2 radians per second, or 0.5 radians per second, or 1.0 radians per second).

In embodiments in which $\omega_{companion}$ has been received from a companion device, $\omega_{companion}$ may be used as an estimate of the magnitude of $\omega_{vehicle}$ (i.e., $\|\omega_{vehicle}\|$) or to improve the estimate derived from the direction of gravity estimated by the wearable (gVec$_{wearable}$). For example, if the unit vector of the steering wheel (steeringColumnUnitVec) has also been estimated, as described above, the magnitude of the steering rotation, $\|\omega_{steering}\|$, may be derived based on the estimate of the magnitude of $\omega_{vehicle}$ as shown in Equation 4:

$$\omega_{wearable} = \|\omega_{steering}\| \cdot \text{steeringColumnUnitVec} + \|\omega_{vehicle}\| \cdot \text{gVec}_{wearable} \qquad (Eq. 4)$$

For example, if the user is not controlling the vehicle, then $\omega_{wearable}$ will be approximately equal to $\|\omega_{vehicle}\| \cdot \text{gVec}_{wearable}$. In contrast, if the user is controlling the vehicle, then the difference between $\omega_{wearable}$ and $\|\omega_{vehicle}\| \cdot \text{gVec}_{wearable}$ that is rotation along the steeringColumnUnitVec will be approximately the magnitude of force attributable to the user's steering motion.

At block 1050, the likelihood that the user is a controller may be estimated. For example, if the magnitude of $\omega_{steering}$ is approximately 0, the likelihood that the user is controlling the vehicle is low, whereas, if the magnitude of $\omega_{steering}$ is greater than 0 (e.g., greater than approximately 0.2 radians per second, or 0.5 radians per second, or 1.0 radians per second), the likelihood that the user is controlling the vehicle is relatively higher (e.g., greater than 50%, 70%, 90% likelihood).

In some embodiments, controller detection method 1000 may end after outputting the estimated likelihood that the user is controlling a vehicle. In other embodiments, the controller detection method 1000 may return to block 1010 (not shown) to refine or otherwise repeat the method of estimating the likelihood that the user is controlling the vehicle.

In some embodiments, other techniques may be used in addition to the techniques described above to improve the confidence in a determination of whether a user is controlling a vehicle. For example, wireless signals based on the distance between the wearable device and the location of the vehicle's antenna may provide a hint as to whether the user is sitting in the controller's position or a passenger's seat.

In some embodiments, the timing between the time at which $\omega_{wearable}$ exceeds the first threshold and the time at which $\omega_{vehicle}$ exceeds the second threshold may also be used to improve the determination of whether a user is controlling a vehicle. For example, if $\omega_{vehicle}$ exceeds the second threshold before $\omega_{wearable}$ exceeds the first threshold, the wearer is not likely to be controlling the vehicle. However, if $\omega_{wearable}$ exceeds the first threshold, followed by $\omega_{vehicle}$ exceeding the second threshold within a period of time consistent with the normal lag between steering motion and vehicle motion, then the wearer is likely to be controlling the vehicle.

As another example, the resting position of the wearable device on a driver may exhibit a higher angle with respect to gravity (e.g., tilt) than that of a passenger. In some embodiments, a time-series analysis of accelerometer or other motion sensor data may enable the wearable device to distinguish between a controller's posture (e.g., hands resting on a steering wheel) and a passenger's posture (e.g., hands resting in the user's lap).

As yet another example, the wearable device may detect whether a user is clenching his or her hand based on data from a heart rate sensor of the wearable device. The wearable device may infer that a user with a clenched hand may be more likely to be a controller than a passenger (e.g., because the controller may be clenching the steering wheel of the vehicle).

As yet another example, the wearable device may be able to measure relatively more intense amounts of noise in the motion due to, for example, bumps or vibrations in the road or other terrain, because a controller is more likely to be gripping the steering wheel, mechanically coupling the wearable device to the steering wheel and chassis of the vehicle.

In some embodiments, the wearable device may receive vehicle information, such as steering angle, wheel speed, or other information, via a vehicle's CANBUS or similar vehicle informatics system.

Figure 11:
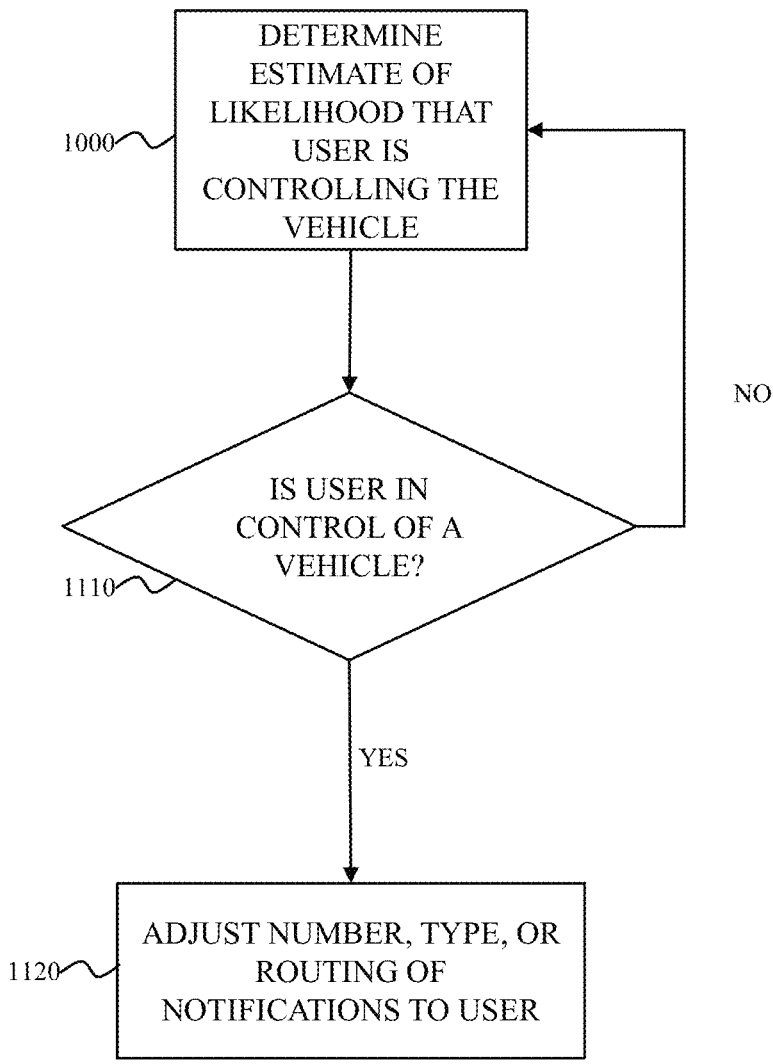
FIG. 11 shows a method for adapting the behavior of a wearable device depending on whether a user is controlling a vehicle in accordance with an embodiment of the present disclosure.

Furthermore, the wearable device may be configured to adapt to whether its user is controlling a vehicle. For example, to reduce potential distractions to a user controlling a vehicle, the wearable device may reduce or eliminate the quantity or type of notifications that would otherwise be presented to the user when the user is not controlling a vehicle. FIG. 11 illustrates one such embodiment.

FIG. 11 shows a method for minimizing notifications to the user based on controller detection in accordance with an embodiment of the invention. Notification adjustment method 1100 may begin at block 1000, which is the controller detection method shown in FIG. 10.

At block 1110, a determination is made whether the user is controlling the vehicle. This determination may be made based on a pre-determined threshold (e.g., a likelihood of more than 75% may be treated as the user being in control of the vehicle), an adaptive threshold (e.g., the likelihood must exceed a threshold adjusted based on other factors described herein, such as sensed noise levels, user hand angle with respect to gravity, or hand clenching, etc.), or based on a heuristic algorithm incorporating as inputs the likelihood a user is controlling the vehicle produced by the method of FIG. 10, sensed noise levels, user hand angle with respect to gravity, hand clenching, and other factors correlated to a user being in control of a vehicle.

If block 1110 determines that the user is not controlling the vehicle, no adjustment is made and the method returns to block 1000 (or waits and then returns to block 1000.) However, if block 1110 determines that the user is controlling the vehicle, notification adjustment method 1100 may proceed to block 1120.

At block 1120, based on the determination that the user is controlling the vehicle, the wearable device adjusts the amount, type, or routing of notifications provided to the user. In some embodiments, notifications are completely prevented while the user is controlling the vehicle. In other embodiments, high priority notifications such as emergency calls are permitted while low priority notifications such as incoming e-mails are suppressed. In some embodiments, the amount and type of notifications prevented from reaching the user may be configured by the user, while in other embodiments it may be controlled by the manufacturer and inaccessible to the user (e.g., to comply with regulatory requirements on driver distraction.) In some embodiments, the wearable device may instead re-route notifications from the device display or speakers to interface elements within the vehicle, such as an in-dash or heads up display or vehicle speakers, rather than preventing notifications from reaching the user.

In some embodiments, other techniques may be used in addition to the techniques described above to adjust the functionality of the wearable device based on the determination that the user is controlling a vehicle. For example, the wearable device may change the way certain gestures or other interactions function when the user is controlling a vehicle. The wearable device may normally recognize a gesture of raising the wearable device and, in response, turn on the display. However, when the user is controlling a vehicle, this gesture may be disabled to avoid confusion with movement related to steering.

As a further example, the wearable device may normally recognize shaking or vibration as a gesture and in response perform an action such as undoing the last action or deleting the most recently received notification. However, when the user is controlling a vehicle, this gesture may be disabled to avoid confusion with movement related to steering, or with vibrations coupling through the vehicle chassis and into a steering wheel and thereby to the wearable device.

The present disclosure is not to be limited in scope by the specific embodiments described herein. Indeed, other various embodiments of and modifications to the present disclosure, in addition to those described herein, will be apparent to those of ordinary skill in the art from the foregoing description and accompanying drawings. Thus, such other embodiments and modifications are intended to fall within the scope of the present disclosure. Further, although the present disclosure has been described herein in the context of at least one particular implementation in at least one particular environment for at least one particular purpose, those of ordinary skill in the art will recognize that its usefulness is not limited thereto and that the present disclosure may be beneficially implemented in any number of environments for any number of purposes.

The invention claimed is:

1. A method comprising:
   receiving, by a wearable device, motion information from a motion sensor of the wearable device;
   determining, by the wearable device using the motion information, that a vehicle is turning, the determining comprising:
   determining an angular velocity of the wearable device;
   estimating the angular velocity of the wearable device attributable to the vehicle; and
   determining that the vehicle is turning in response to the estimated angular velocity exceeding a threshold value of angular velocity;
   estimating a direction of gravity relative to the wearable device based on the motion information from the wearable device;
   determining a turning axis of the vehicle based on the estimated direction of gravity and the motion information from the wearable device; and
   in response to determining that the vehicle is turning, determining, by the wearable device using the motion information, that a user of the wearable device is controlling the vehicle by subtracting angular velocity of the vehicle due to the turning of the vehicle about the turning axis from the determined angular velocity of the wearable device and determining that a difference of the subtracting is greater than zero.

2. The method of claim 1, further comprising adjusting operation of the wearable device while the user is determined to be controlling the vehicle.

3. The method of claim 2, wherein adjusting the operation of the wearable device comprises reducing an amount of notifications routed to a display of the wearable device.

4. The method of claim 2, wherein adjusting the operation of the wearable device comprises the wearable device ignoring a recognized gesture.

5. The method of claim 1, further comprising:
receiving, by a wearable device, motion information from a companion device;
estimating a direction of gravity relative to the companion device based on the motion information from the companion device;
determining a turning axis of the vehicle based on the estimated direction of gravity and the motion information from the wearable device; and
estimating the angular velocity of the vehicle wherein the angular velocity of the vehicle is used to determine that the vehicle is turning.

6. The method of claim 5, wherein a direction of gravity relative to the wearable device is determine based at least in part on the direction of gravity relative to the companion device.

7. The method of claim 1, wherein determining that a user of the wearable device is controlling the vehicle comprises:
receiving, by a wearable device, motion information from a companion device;
estimating an angular velocity of the wearable device not attributable to the motion of vehicle based on the motion information from the wearable device and the motion information from the companion device; and
estimating a likelihood that the user is controlling the vehicle based on the estimated angular velocity of the wearable device not attributable to the motion of the vehicle.

8. The method of claim 1, wherein estimating a direction of gravity relative to the wearable device is not performed when an angular velocity of the wearable device exceeds a first threshold.

9. The method of claim 1, wherein the determination that the user of the wearable device is controlling the vehicle is based at least in part on one or more of a noise level of the motion information, vehicle information received via a vehicle network bus, a sensor detecting a clenched hand of the user, or an angle of a limb of the user on which the wearable device is worn.

10. A wearable device comprising:
a motion sensor for obtaining motion information of a user of the wearable device; and
a processor communicatively coupled to the motion sensor, wherein the processor is configured to;
receive motion information from the motion sensor;
determine, using the motion information, that a vehicle is turning by:
determining an angular velocity of the wearable device;
estimating the angular velocity of the wearable device attributable to the vehicle; and
determining that the vehicle is turning in response to the estimated angular velocity exceeding a threshold value of angular velocity;
estimate a direction of gravity relative to the wearable device based on the motion information from the wearable device;
determine a turning axis of the vehicle based on the estimated direction of gravity and the motion information from the wearable device; and
in response to determining that the vehicle is turning, determine, using the motion information, that the user is controlling the vehicle by subtracting angular velocity of the vehicle due to the turning of the vehicle about the turning axis from the determined angular velocity of the wearable device and determining that a difference of the subtracting is greater than zero.

11. The wearable device of claim 10, wherein the processor is further configured to adjust the operation of the wearable device while the user is determined to be controlling the vehicle.

12. The wearable device of claim 11, wherein adjusting the operation of the wearable device comprises reducing an amount of notifications routed to a display of the wearable device.

13. The wearable device of claim 11, wherein adjusting the operation of the wearable device comprises the wearable device ignoring a recognized gesture.

14. The wearable device of claim 10, wherein the processor is further communicatively coupled to a companion device and wherein the processor is further configured to:
receive motion information from the companion device;
estimate an angular velocity of the wearable device not attributable to the motion of vehicle based on the motion information from the wearable device and the motion information from the companion device; and
estimate a likelihood that the user is controlling the vehicle based on the estimated angular velocity of the wearable device not attributable to the motion of the vehicle, wherein the estimated likelihood that the user is controlling the vehicle is used to determine that the user of the wearable device is controlling the vehicle.

15. The wearable device of claim 10, wherein estimating a direction of gravity relative to the wearable device is not performed when an angular velocity of the wearable device exceeds a first threshold.

16. The wearable device of claim 10, wherein the processor is communicatively coupled to a companion device and wherein the processor is further configured to:
receive motion information from the companion device;
estimate a direction of gravity relative to the companion device based on the motion information from the companion device;
determine a turning axis of the vehicle based on the estimated direction of gravity and the motion information from the wearable device; and
estimate the angular velocity of the vehicle wherein the angular velocity of the vehicle is used to determine that the vehicle is turning.

* * * * *